United States Patent [19]

Pryor et al.

[11] Patent Number: 4,465,374
[45] Date of Patent: Aug. 14, 1984

[54] METHOD AND APPARATUS FOR DETERMINING DIMENSIONAL INFORMATION CONCERNING AN OBJECT

[75] Inventors: Timothy R. Pryor; Omer L. Hageniers; Walter J. Pastorius; Nicholas Liptay-Wagner; Donald A. Clarke, all of Windsor, Canada

[73] Assignee: Diffracto Ltd., Windsor, Canada

[21] Appl. No.: 448,820

[22] Filed: Dec. 10, 1982

Related U.S. Application Data

[60] Continuation of Ser. No. 234,729, Feb. 17, 1981, abandoned, which is a division of Ser. No. 15,792, Feb. 27, 1979, Pat. No. 4,305,661.

[51] Int. Cl.$^3$ .................. G01B 11/12; G01B 11/24
[52] U.S. Cl. .................. 356/375; 356/241; 356/376
[58] Field of Search .......... 356/241, 371, 375–376, 356/378, 384, 387, 390, 394, 4, 381

[56] References Cited

U.S. PATENT DOCUMENTS

| | | | |
|---|---|---|---|
| 3,551,061 | 12/1970 | Glowa | 356/241 |
| 3,667,846 | 6/1972 | Nater et al. | 356/376 |
| 3,749,496 | 7/1973 | Hietanen et al. | 356/241 |
| 3,770,940 | 11/1973 | Harr | 250/203 R |
| 4,042,823 | 8/1977 | Decker et al. | 250/227 |
| 4,199,258 | 4/1980 | Dau | 356/241 |
| 4,266,876 | 5/1981 | Nakazawa et al. | 356/400 |
| 4,281,931 | 8/1981 | Chikama | 356/375 |

FOREIGN PATENT DOCUMENTS

| | | | |
|---|---|---|---|
| 631582 | 1/1962 | Italy | 356/3 |
| 637705 | 12/1978 | U.S.S.R. | 356/241 |

OTHER PUBLICATIONS

Kharizomenov et al., "Photoelectric Instrument for Automatic Measurement of Dimensions In Cutting", Meas. Tech. (USA) vol. 15, #1 (1–72) pp. 47–50.
Vesnina et al., "Instrument for Measuring the Depth of Scratches on Inside Surfaces of Tubes", Soviet Jr. of Optical Technology, vol. 39, 1–72, pp. 33–35.

*Primary Examiner*—William H. Punter
*Attorney, Agent, or Firm*—Larson and Taylor

[57] ABSTRACT

Method and apparatus for determining dimensional information concerning an object. A ring of light is directed onto an object surface such that at least a portion of the ring of light is incident upon the object surface. An image is formed of the incident light reflected from the surface. The width or position of the image is determined. The location of the surface is determined from the image width or position, and dimensional information about the object is determined from the surface location.

15 Claims, 4 Drawing Figures

METHOD AND APPARATUS FOR DETERMINING DIMENSIONAL INFORMATION CONCERNING AN OBJECT

This is a continuation of application Ser. No. 234,729 filed Feb. 17, 1981 and now abandoned, which is a division of our co-pending application Ser. No. 15,792, filed Feb. 27, 1979, now U.S. Pat. No. 4,305,661, the disclosure of which is herein incorporated by reference.

The present invention relates to a method and apparatus for determining dimensional information concerning an object.

A method in accordance with the present invention includes the steps of:
  providing a ring of light;
  directing said ring of light onto an object surface such that at least a portion of said ring of light is incident upon said object surface;
  forming an image of incident light reflected from said surface;
  determining the width or position of said image;
  determining, from the determined width or position of said image, the location of said surface; and
  obtaining, from said surface location, dimensional information concerning said object.

Apparatus in accordance with the present invention comprises:
  means for providing a ring of light;
  means for directing said ring of light onto an object surface such that at least a portion of said ring of light is incident upon said object surface;
  means for forming an image of incident light reflected from said surface;
  means for determining the width or position of said image;
  determining, from the determined width or position of said image, the location of said surface; and
  means for obtaining, from said surface location, dimensional information concerning said object.

There follows a detailed description of preferred embodiments of the invention including the drawings in which.

Figure 1:
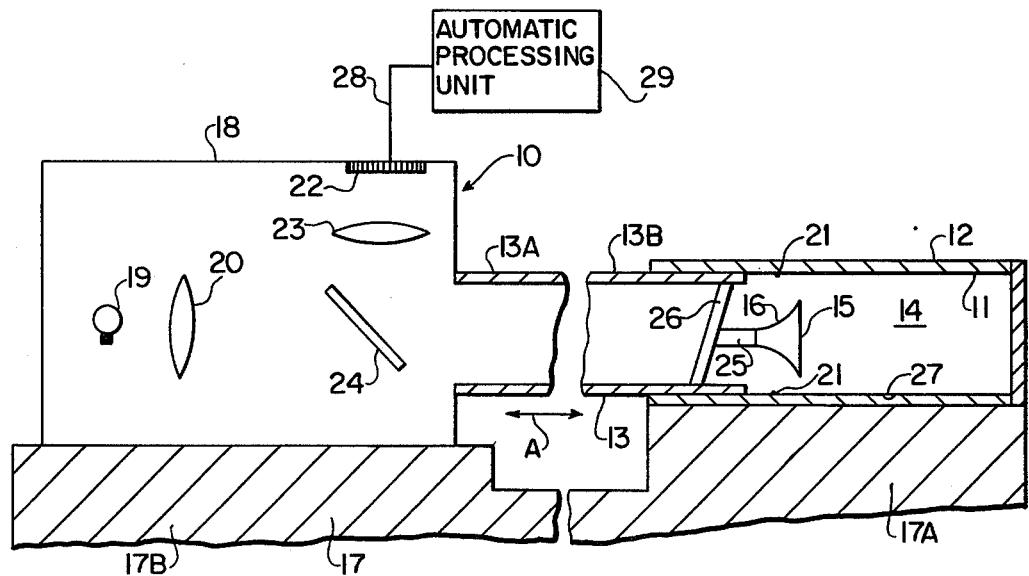
FIG. 1 is a diagrammatic side elevation view, partly in section, of an embodiment of our earlier patent mentioned above which illustrates general physical arrangements which are also applicable to the present invention.

A device 10 for inspecting a bore in accordance with our patent mentioned above is shown in FIG. 1. The bore surface 11 which is to be inspected is the inner cylindrical surface of a tube 12. Tube 11 may be any part, such as a hydraulic brake cylinder, or the like and a simple cylindrical tube is shown for simplicity. It will be assumed for purposes of illustration that the bore is made by a machining operation and it is desired to determine if there are any flaws in the surface in the form of holes resulting from casting or machining. Device 10 includes a probe 13 which is movable axially of bore 14 of tube 12 as shown by arrow A in FIG. 1. The probe is movable in any convenient manner such as by moving the entire device 10 horizontally in the sense of FIG. 1 or by moving the part 12 relative to the device 10. The distal end of the probe carries a mirror 15 having a mirror surface 16 which is in the form of a conical body of revolution. The mirror surface is preferably parabolic or substantially so. The probe is arranged in any convenient manner to move coaxially a pre-determined distance in the tube bore 14. For example, the device may include a table or bed 17 which supports both the tube 12 and a housing 18 which supports probe 13. The device includes suitable clamps or other means to secure housing 18 and tube 11 in the general position shown such that probe 13 may move axially within bore 14. To this end, the device preferably includes means for adjusting the position of the probe and/or housing 18 relative to the position of the piece undergoing inspection. For example, portion 17A of table 17, or which tube 12 is fixedly supported may be movable vertically and horizontally at right angles to arrow A to align the bore and probe. The piece under inspection is positioned adjacent housing 18 such that the probe can move into the bore to an extent necessary to inspect the desired portion of surface 11. In the simplest case, probe 13, secured to housing 18, is moved in by motorized slide 17B in the direction of arrow A under the influence of any suitable control means, not shown.

Light from a source 19 is directed through lens 20 down through the hollow probe and onto parabolic mirror surface 16 of mirror 15 carried at the distal end of probe 13. Light source 19 is conveniently a conventional halogen bulb. The mirror is designed to focus the light onto bore surface 11 in the form of a bright circumferential ring denoted as 21 in FIG. 1. The bright ring of light is reflected back down the probe tube by mirror surface 16 and is imaged upon a light detector array 22 by means of a lens 23 via a beam splitter 24. The light detector array in this embodiment is preferably circular in view of the circular format of the light reflected from bore surface 11. An example of a suitable array is a circular, self-scanning photodiode array. For example, a commercially available circular array with a mean diameter of 0.28 inches and having 720 photodiode elements arranged on one half degree centers is suitable. Mirror surface 16 is preferably designed to focus the incident light on the bore surface to provide an intense bright ring of light which is readily detected by the photodiodes in array 22. Mirror 16 is secured in position at the distal end of probe 13 in any convenient manner such as by a mounting member 25 secured to mirror 16 and to a transparent member 26, preferably glass, fixedly mounted in tube 13. Glass member 26 is preferably inclined to the probe axis to reduce reflection of incident light back to detector array 22.

In use, test piece 12 is positioned on table portion 17A such that probe 13 moves coaxially within bore 14. In use, as the probe is axially translated through the bore length, each successive portion of the bore length is sequentially scanned by the array which can operate, typically, with speeds of several thousand scans per second. This allows an extremely quick scan of the bore with considerable detail. For example, in the case of a seven inch bore having a diameter of 1.7 inches, the bore can be scanned in about one second with every detector of the array reading a zone of approximately 0.007 inches×0.030 inches (approximately) on any one scan. Obviously, resolution can be increased or decreased by using different detector arrays and by changing the lens magnification. For example, in the system described above, the bore diameter is 1.7 inches and the diameter of the circular array is 0.28 inches. If the diameter of the array were increased to, e.g., 1.7 inches, and the width of the individual detectors kept the same, the number of detectors would increase from 720 to over 4000 and resolution would increase correspondingly. Of course, in that instance, lens 23 would be adjusted to image the reflected light on the larger array. Lens 23 and the other optical elements of the system are thus preferably adjustable to accomodate various applications of the device.

The light reflected from the bore surface readily displays physical features such as directs, holes, depressions, ridges, bumps, and the like present in the illuminated area of the bore surface. These show up as zones of differing intensity in the reflected light. The size and intensity of those zones depends, of course, on the extent and nature of the physical characteristics of the surface on which the focussed light is incident. In the illustrated case, in which the bore is machined, it is desired to detect flaws in the form of depressions such as porosity pit 27 shown exaggerated in size in FIG. 1. These flaws are indicated by a substantial reduction in reflected light. In some instances, such as where the flaw is large, the defect can be detected by examination of the reflected light by the unaided eye. For example, holding the probe in fixed position with the light incident on a defect such as hole 27, a dark spot in the reflected light ring on a viewing screen. An object of the invention, however, is to provide a rapid and dependable method of inspecting bores and the like and this is accomplished in accordance with our patent mentioned above, by automatically examining the reflected light in an appropriate processing unit in which a comparison is made between the light reflected from a portion of the bore surface with the light reflected from a known standard bore surface and/or further portions of the bore surface at locations on either side of and proximate to the first mentioned portion of the bore. In the usual case, the portion under investigation is the zone from which reflected light is received by an individual detector in an array, although the portion under investigation may be longer. Further, in the usual case, the further portions used for comparison purposes each constitute a zone on the bore surface from which reflected light is received by at least one individual detector. It is important that the analysis of the reflected light takes into account variations in light level around the bore surface due to various factors such as dirtiness of the bore, mis-alignment of the probe within the bore (e.g. not truly co-axial) or other characteristics of the bore which are not flaws of the type desired to be detected but which nevertheless can cause changes in reflected light level. Accordingly, the electrical output signals 28 from detector array 22 are directed into automatic processing unit 29.

As mentioned above, photo detector array 22 is commercially available. These arrays are available in many configurations and can be readily obtained commercially. Most detector arrays employ solid state, light sensitive elements such as photodiodes, although other elements such as photosensitive transistors could be used. Photo array video comceras having a square matrix of 128×128 photosensitive elements are the General Electric Model TN 220 and TN 2201 video cameras. Other commercially available photo arrays include linear arrays and rectangular matrix arrays. Furthermore, any type of video camera can be used, including the continuous raster sweep type that is used in conventional television. Naturally, the specific circuitry in a particular automatic processing unit has to be compatible with the particular type of video detector.

Figure 2A:
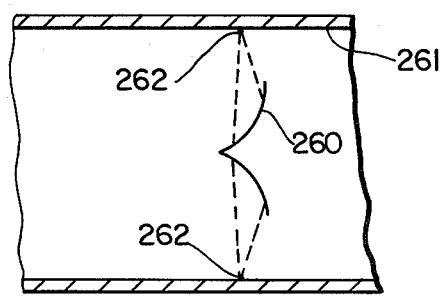
FIG. 2A is a diagrammatic side elevation view, partly in section, illustrating a portion of an embodiment of the invention.
Figure 2B:
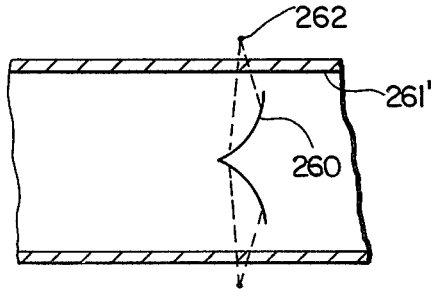
FIG. 2B is a diagrammatic side elevation view, partly in section, illustrating the embodiment of FIG. 2A under different conditions.

An arrangement such as that shown in FIG. 1 may also be utilized to determine the size of objects, bores, and the like. Consider, for example, the convergence of the rays from the parabolic mirror 260 shown in FIG. 2A. It is clear that if the part surface, such as bore surface 261, is at the focus, the width of the projected spot 262 in the axial direction at the part surface would be minimal. However, if the bore diameter decreases (as shown in FIG. 2B) or increases, the width of the illuminated portion of the surface 261' will be spread accordingly. The imaging lens does not focus such light onto a linear array in the radial direction. This system can thus be used to map out the width of the line and, accordingly, achieve a degree of dimensional data about the surface of the part. It also can be used to look for flaws therein. To sweep the linear detector array, means may be provided to rotate the image on its face and for this purpose an image rotating circuit can readily be provided. For example, a rotating dove prism 452 (FIG. 3) may be employed wherein the image rotates for every 180° of rotation.

Naturally, another way of scanning the 360° is to rotate the arrays themselves although this is considered cumbersome and cannot be done at anywhere near the speed achieved by rotating the image on the array. Another version would utilize a square diode array or perhaps a special diode array with numerous linear scanning elements. While these do not exist at this time, their future existence can be hypothesized and they would be ideal for the purpose. As mentioned above, this system can be used to map out the width of the line and provide dimensional data about the bore surface. Since the width of the spot on the bore surface will vary with the distance of the bore surface from the optical axis, the spot width data or the mapped-out spot width data can be used to determine diameter, roundness, ovality and the like. Moreover, as the probe moves relatively axially of the bore, this information can be provided along the bore length, thus enabling a determination of, e.g., cylindricity.

Figure 3:
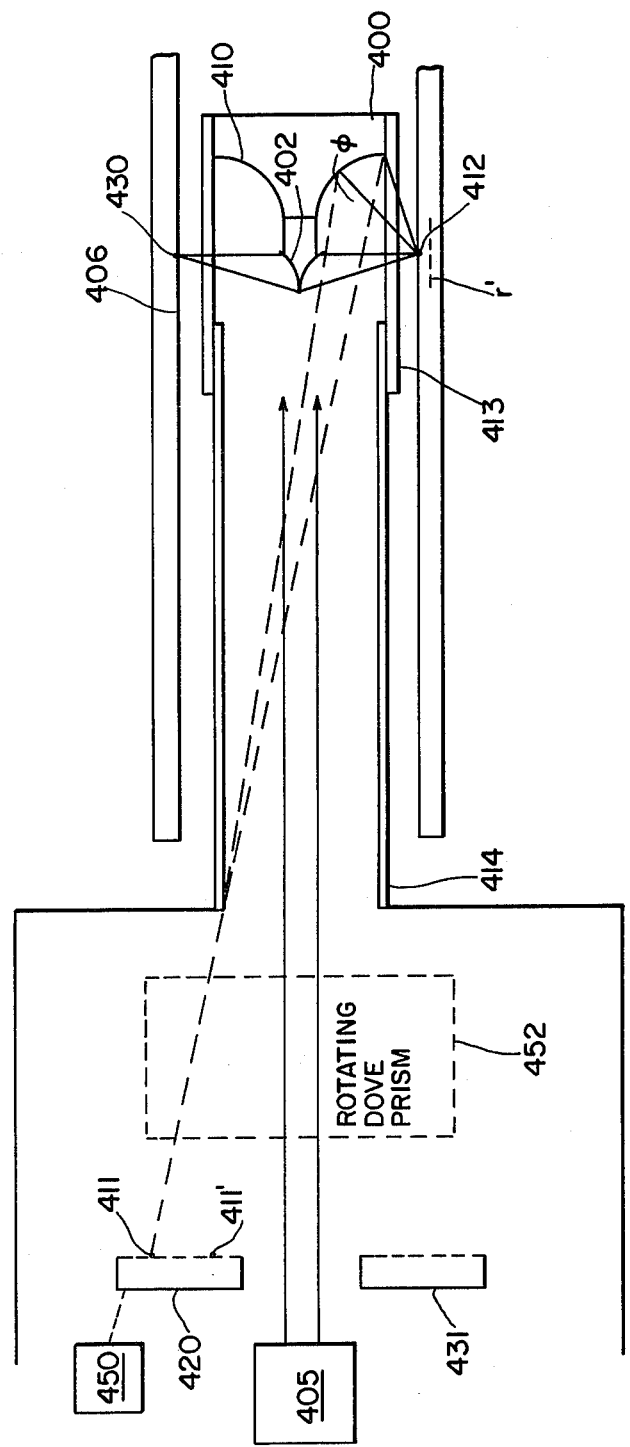
FIG. 3 is a diagrammatic side elevation view, partly in section, illustrating apparatus in accordance with the invention.

FIG. 3 illustrates an alternative size determination embodiment also capable of 360° bore roundness and diameter determination, a revolutionary non-contact capability.

As shown, a two angle mirror, 400, like that of FIG. 7 of our patent mentioned above, is utilized. However, two spherical curvature figures of rotation are preferably used: section 402 to approximately focus incoming light such as beam from laser 405 onto the bore wall 406 to be inspect and section 410 used to form an image 411 of the spot 412 on the bore. Cylindrical glass tube 413 is used to attach the mirrors to probe housing 414. As mentioned above, dove prism 452 may be employed to rotate the image for every 180° of rotation of the prism.

Because of the included angle between the two reflective surfaces, a different bore radius r' causes image 411 to fall in a different position 411'. Thus, monitoring of image position with photodiode array 420 provides a measure of bore dimension.

The same set-up is obviously capable of providing diameter information using opposite spot 430 projected onto the bore wall and imaged onto second array 431 in a like manner. It is noted that a laser source is preferred because of the lack of chromatic aberation where lenses are used and the ability to project intense light into a small area.

Analysis circuit 450 finds the centroid of each image spot as disclosed in our patent mentioned above, independent of power deviation on the bore wall, to give accurate diameter information. Note that other lenses or mirrors can be used to further magnify the change in location of the image spots for bore diameter differences.

A big feature of the embodiment of FIG. 3, is that the image spot is actually a ring if the mirror section shown is a 360° figure of revolution. Thus, rotation of the one or both of the arrays gives 360° roundness, ovality and concentricity information as the probe is moved down the bore. This is a capability not possible in any other gage capable of operation at production rates.

It should be noted that incorporation of an image rotator 452, for example a dove prism, allows the 360° ring images to sweep fixed array positions, thus providing an extremely fast scan, for example ten bore sweeps/sec., which, with the array running at 3600 radial scans/sec., gives dimensional data every degree as to diameter or radius. This speed allows real time calculation of true bore cylindricity, and further provides for finding defects in the bore and actually dimensionalizing their depth. It also allows land locations, portholes, etc. to be spotted in the bore and measured exactly, assuming forward movement of the probe is encoded.

Note that when bore surface is located at a larger radius 4' (dotted lines), spot 411 moves to position 411' with considerable magnification.

What is claimed is:

1. A method of determining the diameter of an object with a cylindrical surface comprising the steps of:
   providing a ring of light around the cylindrical surface, said ring having a center located along the longitudinal axis of the cylindrical surface;
   focusing said ring of light onto the cylindrical surface such that at least a portion of said ring of light is focused upon a small area of the cylindrical surface;
   forming an image of incident light reflected from the cylindrical surface;
   determining the longitudinal width of said image;
   determining, from the determined width of said image, the location of said cylindrical surface; and
   obtaining, from said surface location, the diameter of the cylindrical surface.

2. A method according to claim 1 wherein said ring of light is focused onto said object surface by a mirror.

3. A method according to claim 1 wherein said image of light reflected from said surface is reflected by a mirror.

4. A method according to claim 1 wherein said incident light image is formed on a photodiode array.

5. A method according to claim 1 wherein said step of determining the width of said image comprises determining the width of a plurality of discrete portions of said image.

6. A method according to claim 5 wherein said discrete portions of said image are diametrically opposite one another.

7. A method according to claim 6 wherein said object surface comprises a bore surface.

8. A method according to claim 1 wherein the image of said light reflected from said surface is rotated.

9. Apparatus for determining the diameter of an object with a cylindrical surface comprising:
   means for providing a ring of light around the cylindrical surface, said ring having a center located along the longitudinal axis of the cylindrical surface;
   means for focusing said ring of light onto the cylindrical surface such that at least a portion of said ring of light is focused upon a small area of said cylindrical surface;
   means for forming an image of incident light reflected from said cylindrical surface;
   means for determining the longitudinal width of said image;
   means for determining, from the determined width of said image, the location of said cylindrical surface; and
   means for obtaining, from said surface location, the diameter of the cylindrical surface.

10. Apparatus according to claim 9 further comprising mirror means for focusing said ring of light onto said object surface.

11. Apparatus according to claim 9 comprising mirror means for reflecting said image of light from said surface.

12. Apparatus according to claim 9 comprising a photodiode array on which said light image is formed.

13. Apparatus according to claim 9 wherein means for determining the width of said image comprises means for determining the width of a plurality of discrete portions of said image.

14. Apparatus according to claim 13 wherein said discrete portions of said image are diametrically opposite one another.

15. Apparatus according to claim 9 wherein the image of said light reflected from said surface is rotated.

* * * * *